US007304029B1

(12) United States Patent
Scheepens et al.

(10) Patent No.: US 7,304,029 B1
(45) Date of Patent: Dec. 4, 2007

(54) NEUROPROTECTIVE EFFECT OF GROWTH HORMONE

(75) Inventors: Arjan Scheepens, Maastricht (NL); Christopher E. Williams, Auckland (NZ); Peter David Gluckman, Auckland (NZ); Ross Graham Clark, Auckland (NZ)

(73) Assignee: Neuren Pharmaceuticals Ltd., Auckland (NZ)

( * ) Notice: Subject to any disclaimer, the term of this patent is extended or adjusted under 35 U.S.C. 154(b) by 0 days.

(21) Appl. No.: 09/786,982

(22) PCT Filed: Sep. 3, 1999

(86) PCT No.: PCT/NZ99/00147

§ 371 (c)(1),
(2), (4) Date: Feb. 27, 2002

(87) PCT Pub. No.: WO00/13650

PCT Pub. Date: Mar. 16, 2000

(30) Foreign Application Priority Data

Sep. 3, 1998 (NZ) ..................................... 331719

(51) Int. Cl.
*A61K 38/18* (2006.01)
*A61K 38/25* (2006.01)
*A61K 38/27* (2006.01)
*A61K 38/30* (2006.01)
*A61K 38/31* (2006.01)

(52) U.S. Cl. ..................... 514/2; 514/3; 514/4; 514/12; 530/399

(58) Field of Classification Search ............... None
See application file for complete search history.

(56) References Cited

U.S. PATENT DOCUMENTS

| 4,939,124 A | 7/1990 | Cacabelos |
| 5,468,726 A | 11/1995 | Cacabelos |
| 5,736,515 A | 4/1998 | Bengtsson |
| 2003/0049838 A1 | 3/2003 | Thompson et al. |

FOREIGN PATENT DOCUMENTS

| AU | 757907 | 6/2003 |
| EP | 0720483 | 9/1993 |
| WO | WO 99/33481 | 7/1999 |
| WO | WO 00/13650 | 3/2000 |
| WO | WO 03/24471 | 3/2003 |

OTHER PUBLICATIONS

Rudinger, In *Peptide Hormones*, Ed. J. A. Parsons, University Park Press, Baltimore, pp. 1-7, 1976.*
Burman et al, *Clinical Endocrinology*, vol. 44, pp. 319-324, 1996.*
Nyberg et al. *Horm. Res.* vol. 45, pp. 18-22, 1996.*
Golab et al. *Endokrynologia Polska*, vol. 14, pp. 233-237, 1963.*
Golab et al. *Endokrynologia Polska*, vol. 14, pp. 233-237, 1963. (English Translation).*
Phelps, C.J., "Stimulatory Effect of Human, But Not Bovine, Growth Hormone Expression on Numbers of Tuberoinfundibular Dopaminergic Neurons in Transgenic Mice," *Endocrinology*, Baltimore, Maryland, 1977, Vo. 138, No. 7, pp. 2849-2855.
Chen, L. et al., "Growth Hormone, Insulin-like Growth Factor I, and Motoneuron Size," *Journal of Neurobiology*, 1997, vol. 32, No. 2, pp. 202-212.
Scheepens, A., et al., "Alterations in the Neural Growth Hormone Axis Following Hypoxic-Ischemic Brain Injury," *Molecular Brain Research*, Elsevier Science BV, Amsterdam, Netherlands, 1999, vol. 68, pp. 88-100.
Scheepens, A., et al., "Growth Hormone as a Neuronal Rescue Factor During Recovery from CNS Injury,"*Neuroscience*, Jun. 14, 2001, vol. 104, No. 3, pp. 677-687.
Clark, Ross G. and Iain Robinson, "Up and Down the Growth Hormone," *Cytokine & Growth Factor Reviews*, 1996, vol. 7, No. 1, pp. 65-80.
Lobie, Peter E.; García Aragòn, Juanita; Lincoln, David T.; Barnard, Ross; Wilcox, Josiah N.; and Waters, Michael J., "Localization and Ontogeny of Growth Hormone Receptor Gene Expression in the Central Nervous System," *Developmental Brain Research*, Elsevier Science Publishers B.V., 1993, vol. 74, pp. 225-233.
Loccick, Sarah A.; Xin-Jun Liu; Lu, Zi-Xian; Liu, Changlu; Behan, Dominic P.; Chalmers, Derek C.; Foster, Alan C.; Vale, Wylie W.; Ling, Nicholas; and De Souza, Errol B., "Displacement of Insulin-like Growth Factors from Their Binding Proteins as a Potential Treatment for Stroke," *Pharmacology*, The National Academy of Sciences, Feb. 1998, vol. 95, pp. 1894-1898.
L. Chen, et al., "Growth Hormone, Insulin-like Growth Factor I, and Motoneuron Size", Dept. of Physiology and Curriculum in Neurobiology, N.C., Sep. 25, 1996, pp. 202-212.
Anatomy, Tulane Univ. School of Medicine, Endocrinology, vol. 138, No. 7, pp. 2849-2855, 1997.
R. Clark, et al., "Up and Down the Growth Hormone Cascade", Cytokine & Growth Factor Reviews, vol. 7, No. 1, pp. 65-80, 1996.
Pharmacology, vol. 95, pp. 1894-1898, Feb. 1998.
P. E. Lobie, et al., "Localization and ontogeny of growth hormone receptor gene expression in the central nervous system", Developmental Brain Research, 74 (1993) 225-233.

\* cited by examiner

*Primary Examiner*—Christina Chan
*Assistant Examiner*—Stephen Gucker
(74) *Attorney, Agent, or Firm*—Borson Law Group, PC; D. Benjamin Borson

(57) ABSTRACT

The invention relates to neuroprotection and to medicaments for use therein. Neuroprotection is induced by activation of neural growth hormone receptors, primarily using medicaments comprising growth hormone, growth hormone analogs or ligands which are functionally equivalent. Such medicaments may also include one or more secondary neuroprotective agents.

7 Claims, 3 Drawing Sheets

Effect of ICV rat GH treament on serum and CSF IGF-1 levels following moderate HI Effect of ICV rat GH treatment on neuronal score following moderate HI

NEUROPROTECTIVE EFFECT OF GROWTH HORMONE

This invention relates to neuroprotection. In particular, it relates to a new therapeutic use of growth hormone, its analogs and functionally equivalent ligands in neuroprotection.

BACKGROUND

The presence of growth hormone receptor/binding protein (GHR/BP) has been reported in both the juvenile (Lobie et al (1993)) and adult (Burton et al (1992)) rat brains, and its pattern of distribution appears to be widespread, especially in the juvenile CNS. The ontogeny of expression of the GHR/BP also appears to be similar to IGF-1 and the IGF-1 receptor expression in the developing CNS, being produced mainly in fetal and early post-natal life and declining thereafter (Bartlett et al (1991), Bondy and Lee (1993), Garofalo et al (1989)). Studies of transgenic mice have showed that both IGF-1 knockout and growth hormone deficient mice exhibit hypomyelinated, microcephalic brains (Beck et al (1995), Noguchi (1991)), thus indicating a role for both growth hormone and IGF-1 in brain growth, development and myelination. A recent study in growth hormone-deficient children has shown a striking correlation between hypothalamic disturbances influencing growth hormone secretion and their relative score in a visual motor psychological test, indicating a link between an abnormal somatotropic axis and reduced cognitive performance (Andronikof-Sanglade et al (1997)).

There has however to date been no demonstration of a neuroprotective function for growth hormone. (By "neuroprotective" is meant exhibiting neuroprophylactic and/or neuronal rescue capabilities in the CNS). While U.S. Pat. No. 4,791,099 does describe the symptoms of central nervous system diseases as being treatable with a combination of growth hormone and androgens, there is no teaching of administering growth hormone alone. Certainly, there is no teaching in U.S. Pat. No. 4,791,099 of growth hormone as having other than an anabolic effect to render patients treated more receptive to the restorative effects of the androgens. No neuroprophylactic or neuronal rescue capabilities are suggested.

It is the applicant's finding that growth hormone is itself neuroprotective. This finding is surprising in spite of the somatotropic axis relationship between growth hormone and IGF-1 and the demonstration that IGF-1 has neuronal rescue capabilities, both in vitro and in vivo (see Knusel et al (1990), Guan et al (1993)). That is because IGF-1 acts through the IGF-1 receptor whereas growth hormone does not. Thus, growth hormone is neuroprotective in the thalamus, where there is reported distribution of growth hormone receptor immunoreactivity (Lobie et al (1993) *Developmental Brain Research* 74: 225) but not in the striatum, whereas IGF-1 is neuroprotective in the striatum, where IGF-1 receptors have been reported to be present (Hill et al (1986) *Neuroscience* 17:1127; Lesinak et al (1988) *Endocrinology* 123:2089)) but not in the thalamus. Furthermore and as the applicants have found that growth hormone administered centrally to the brain is neuroprotective without effecting a concurrent increase in IGF-1 levels.

It is these surprising findings upon which the present invention is based.

SUMMARY OF THE INVENTION

In a first aspect, the present invention provides a method for inducing a neuroprotective effect in the brain of a patient which comprises the step of administering growth hormone, an analog thereof or a functionally equivalent ligand to the brain of said patient.

As used herein, "analog" means a fragment or variant of an active agent which has at least substantially equivalent biological activity to that active agent.

The term "functionally equivalent ligand" means an agent which binds to and activates the neural receptors in the brain which growth hormone binds to and activates.

In a further aspect, the invention provides a method for inducing a neuroprotective effect in the brain of a patient which comprises the step of increasing the effective concentration of growth hormone or a functionally equivalent endogenous ligand in the brain of said patient.

Preferably, the effective concentration of said growth hormone/analog/ligand is increased through direct administration.

Alternatively, the effective concentration of growth hormone or ligand is increased through administration of an agent which either stimulates production of growth hormone or the ligand or which lessens or prevents inhibition of growth hormone/ligand activity.

Preferably, the neuroprotective effect is a neural rescue effect.

Alternatively, the neuroprotective effect is a neuroprophylactic effect.

In a further embodiment, the invention provides a method of treating a patient to rescue neurons otherwise destined to die as the result of a prior neuronal insult which comprises the step of increasing the effective amount of growth hormone, an analog thereof or a functionally equivalent ligand in the brain of said patient.

As used herein, "neuronal insult" is used in its broadest possible sense and includes neuronal insults due to trauma (injuries), degenerative diseases and disorders, motor diseases and disorders, demyelinating diseases and disorders, neurological syndromes, eye diseases and sleep disorders.

The applicants have found that the neuroprotective role of growth hormone is mediated through the neural growth hormone receptors. By "neural growth hormone receptor" is meant any receptor found in the brain which growth hormone binds to and/or activates or to which growth hormone is capable of binding/activating. Such receptors include growth hormone receptor (GHR) and prolactin receptor (PRL-R).

Therefore, in a further aspect the invention provides a method for inducing a neuroprotective effect in the brain of a patient which comprises the step of causing an increase in the activity of neural growth hormone receptors in the brain of said patient.

Preferably, the increase in activity is the result of direct administration to the brain of said patient of an agent which increases the activity of said neural growth hormone receptors.

Preferably, said agent is one which binds growth hormone receptors directly. Such an agent can be growth hormone, an analog thereof or a functionally equivalent ligand such as prolactin, an analog of prolactin, placental lactogen or an analog of placental lactogen.

Alternatively, the agent is one which effects an increase in the active concentration of an agent which binds neural growth hormone receptors (ie. the agent administered acts indirectly). Preferably, such an agent is selected from growth hormone releasing proteins (GRP), growth hormone releasing hormone (GHRH), functionally equivalent secretagogues of these and somatostatin release inhibitory factor (SRIF).

Conveniently, the method is neuroprophylactic.

Alternatively, said method induces a neural rescue effect.

In still a further aspect, the invention provides a method of treating a patient to rescue neurons otherwise destined to die as the result of a prior neuronal insult which comprises the step of causing an increase in the activity of neural growth hormone receptors in the brain of said patient.

The applicants also contemplate a combination therapy in which growth hormone or an analog/ligand thereof can be administered to rescue a first population of neuronal cells and a second neuroprotective agent can be administered to protect a second population of neuronal cells. The invention therefore further provides a method of treating a patient to protect neurons which comprises administering growth hormone, an analog thereof or a functionally equivalent ligand in combination with an additional neuroprotective agent.

Preferably, the additional neuroprotective agent is selected from IGF-1, GPE, activin, NGF, TGF-β growth hormone binding proteins, IGF-binding proteins and bFGF.

Conveniently, the method induces a neuronal rescue effect to rescue neurons otherwise destined to die as the result of neuronal insult.

In one embodiment, the insult is Huntington's disease or Alzheimer's disease and said growth hormone/analog/ligand is administered in combination with one or more of GPE, IGF-1 and activin.

In a further embodiment, the insult is corticobasal degeneration or Steele-Richardson-Olszewski syndrome and said growth hormone/analog/ligand is administered in combination with IGF-1.

In another embodiment, the insult is Devic's disease or Pick's disease and said growth hormone/analog/ligand is administered in combination with one or both of GPE and IGF-1.

In another embodiment, the insult is diabetic neuropathy and said growth hormone/analog/ligand is administered in combination with one or both of activin and IGF-1.

In still a further aspect, the invention provides a medicament for use in treating a patient to rescue neurons otherwise destined to die as the result of a prior neuronal insult which comprises, in combination, growth hormone, an analog thereof or a functionally equivalent ligand and one or more selected secondary neuroprotective agents other than IGF-1, preferably one or more of GPE, activin, NGF, TGF-β, a growth hormone binding protein, an IGF binding protein and bFGF.

Preferably, said medicament further includes IGF-1.

In yet a further aspect, the invention provides the use of growth hormone or an analog thereof or a functionally equivalent ligand in the preparation of a neuroprotective medicament.

Preferably, said medicament is for use in rescuing neurons otherwise destined to die as the result of neuronal insult.

DESCRIPTION OF THE DRAWINGS

While the present invention is broadly defined above, those persons skilled in the art will appreciate that it is not limited thereto and that it further includes embodiments of which the following description provides examples. In addition, the invention will be better understood through reference to the accompanying drawings in which.

DESCRIPTION OF THE INVENTION

Figure 1:
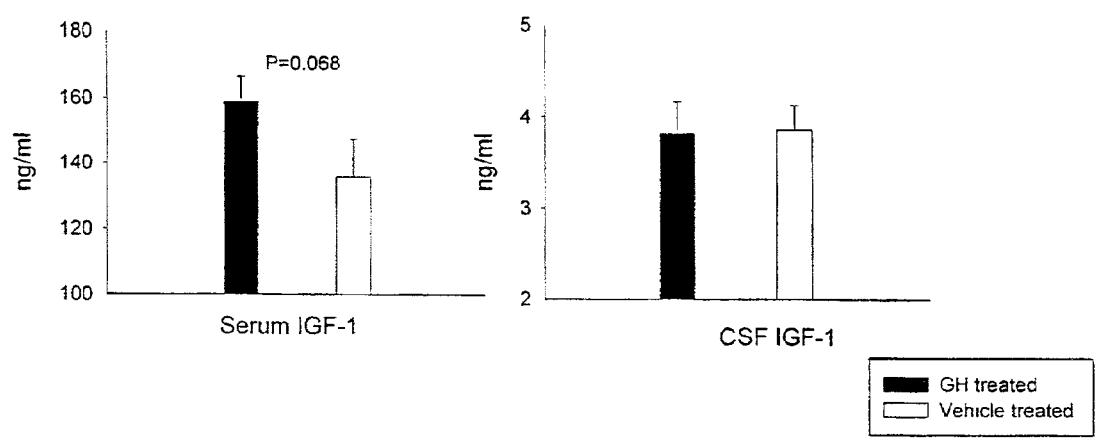
FIG. 1 shows the effect of ICV rat growth hormone treatment on serum and CSF IGF-1 levels following moderate HI.

As broadly defined above, the present invention relates to neuroprotection. This is both in the sense of neuroprophylaxis and neuronal rescue, with the focus being on rescue.

The applicants have found that neuroprotection and in particular neuronal rescue is able to be effected using two approaches. The first approach is through a focus upon growth hormone, its analogs and functionally equivalent ligands. The applicants have found that increasing the effective concentration of growth hormone, its analogs or functionally equivalent ligands within the brain of a patient induces a neuroprotective effect and in particular a neuronal rescue effect.

The growth hormone which is used in this approach can be any mammalian growth hormone, with examples being human growth hormone, rat growth hormone and porcine growth hormone. It is however preferred that the growth hormone employed 30 be human growth hormone where the patient is a human.

The growth hormone which is used in the present invention can be in its substantially purified, native, recombinantly produced, or chemically synthesized forms. For example, the growth hormone can be isolated directly from blood, such 35 as from serum or plasma, by known methods. See, for example, Phillips (1980) *New Eng J. Med* 302:371-380; Svoboda et al (1980) *Biochemistry* 19:790-797; Cornell and Boughdady (1982) *Prep. Biochem.* 12:57; Cornell and Boughdady (1984) *Prep. Biochem.* 14:123; European Patent No. EP 123,228; and U.S. Pat. No. 4,769,361. Alternatively, growth hormone can be synthesized chemically, by any of several techniques that are known to those skilled in the peptide art. See, for example, Li et al (1983) *Proc. Natl. Acad. Sci.* USA 80:2216-2220, Stewart and Young (1984) *Solid Phase Peptide Synthesis* (Pierce Chemical Company, Rockford, Ill., USA) and Barany and Merrifield (1980) The peptides: Analysis, Synthesis, *Biology*, ed. Gross and Meienhofer, Vol 2 (Academic Press, New York, 1980), pp 3-254, for solid phase peptide synthesis techniques; and Bodansky (1984) Principles of Peptide Synthesis (Springer-Verlag, Berlin); and Gross and Meienhofer, eds (1980) The Peptides: Analysis, Synthesis, *Biology*, Vol 1 (Academic Press, New York, USA) for classical solution synthesis. Growth hormone can also be chemically prepared by the method of simultaneous multiple peptide synthesis. See, for example, Houghten (1985) *Proc. Natl. Acad. Sci*, USA 82:5131-5135 and U.S. Pat. No. 4,631,211.

Genetic engineering by recombinant DNA techniques can be the most efficient way of producing the growth hormone. The human DNA sequence encoding these proteins is known and can be introduced into host cells for expression. The proteins can be produced by recombinant DNA techniques in *E. coli*, yeast, insect and mammalian cells. A secreted polypeptide can be made by adding a signal sequence to the DNA sequence encoding the neurologic therapeutic. In addition, the DNA sequence can be modulated to make fragments, analogues, or derivatives. Such recombinant DNA techniques are generally available in the art.

Most conveniently, the effective concentration of growth hormone will be increased through direct administration using either growth hormone itself or a growth hormone pro-drug (a form which is cleaved within the body to release growth hormone). It is however not the applicants intention to exclude increasing growth hormone concentration through administration of either growth hormone agonists or secretagogues (substances which effect a direct increase in production of growth hormone within the brain (eg. growth hormone releasing peptides (GHRP) such as GHRP-1, GHRP-2, GHRP-6, Hexarelin, G-7039, G-7502, L-692,429, L-692,585, L-163,191 [Deghenghi et al. (1994) *Life Sci.* 54:1321; Bowers (1993) *J. Paed Endocrinol.* 6:21; Smith et al. (1993) *Science* 260:1640; McDowell et al. (1995) *Proc. Natl. Acad. Sci. USA* 92:11165; Patchett et al. (1995) *Proc. Natl. Acad. Sci. USA* 92:7001; Clark and Robinson (1996) *Cytokine and Growth Factor Reviews* 7(1):65]1 or growth hormone releasing hormone (GHRH) [Frohman et al. (1992) *Front Neuroendocrinol.* 13:344; Clark and Robinson (1996) *Cytokine and Growth Factor Reviews* 7(1):65] or inhibitors of growth hormone antagonists (substances which bind growth hormone or otherwise prevent or reduce the action or production of growth hormone within the body). These latter compounds exert an indirect effect on effective growth hormone concentrations through the removal of an inhibitory mechanism, and includes substances such as somatostatin (somatotropin release inhibitory factor (SRIF)) [Gillies (1997) Trends in Pharmacol. Sci. 18(3):87].

Another administrable form is a replicable vehicle encoding growth hormone. Such a vehicle (which may be a modified cell line or virus which expresses growth hormone within the patient) has the capability of increasing the concentration of growth hormone within the patient for a prolonged period. [Maxwell et al (1998) *Neurosurgery* 43(5): 1157] Such a vehicle can form part of a brain implant.

In addition to growth hormone itself, the use of analogs of growth hormone or functionally equivalent ligands of growth hormone is contemplated.

As used herein, "analog" means a protein or peptoid which is a variant of growth hormone through modification (such as by insertion, deletion or substitution of one or more amino acids, glycosylation, phosphorylation or addition of one or more foreign moieties) but which retains at least substantial functional equivalency.

A protein is a functional equivalent of another protein for a specific function if the equivalent protein is immunologically cross-reactive with, and has at least substantially the same function as, the original protein. The equivalent can be, for example, a fragment of the protein, such as a C-terminal or N-terminal deletion, a fusion of the protein with another protein or carrier, or a fusion of a fragment with additional amino acids. For example, it is possible to substitute amino acids in a sequence with equivalent amino acids using conventional techniques. Groups of amino acids normally held to be equivalent are:

(a) Ala, Ser, Thr, Pro, Gly;
(b) Asn, Asp, Glu, Gln;
(c) H is, Arg, Lys;
(d) Met, Leu, Ile, Val; and
(e) Phe, Tyr, Trp.

Functionally equivalent proteins will generally have at least 70%, preferably at least 80%, more preferably about 90% to 95% or more, and most preferably about 98% or more amino acid sequence identity to the amino acid sequence of the reference molecule. By "reference molecule" is intended a sequence used for comparison which may be either a complete sequence or a subset of the specified sequence. By "sequence identity" is intended the same amino acid residues are found within the variant and the reference molecule when a specified, contiguous segment of the amino acid sequence of the variant is aligned and compared to the amino acid sequence of the reference molecule.

For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous nucleotides, and may be 30, 40, 50, 100 or more nucleotides. Corrections for increased sequence identity associated with inclusion of gaps in the variant's amino acid sequence can be made by assigning gap penalties. Methods of sequence alignment are well known in the art.

The determination of percent identity between two sequences can be accomplished using a mathematical algorithm. A non-limiting example of a mathematical algorithm utilized for the comparison of sequences is the algorithm of Myers and Miller (1988) *CABIOS* 4:11-17. Such an algorithm is incorporated into the ALIGN program version 2.0), which is part of the GCG sequence alignment software package. When utilizing the ALIGN program for comparing amino acid sequences, a PAM120 weight residue table, a gap length penalty of 12, and a gap penalty of 4 can be used. An additional preferred program is the Pairwise Alignment Program (Sequence Explorer), using default parameters. Another non-limiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad Sci. USA* 90:5873-5877. Such an algorithm is incorporated into the NBLAST and XBLAST programs of Altschul et al (1990) *J. Mol. Biol.* 215:403. Nucleotide sequences homologous to the growth hormone nucleic acid molecules of the invention can be obtained using BLAST nucleotide sequences performed with the NBLAST program, score=100, wordlength=12. BLAST protein searches can be performed with the XBLAST program, score=50, wordlength=3, to obtain amino acid sequences homologous to growth hormone protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (eg. XBLAST and NBLAST) can be used. See http:/www.ncbi.nlm.nih.gov.

Functional equivalency of growth hormone analogs can also be readily screened for by reference to the ability of the analog to both bind to and activate the appropriate receptor. In this case, the receptor is a neural growth hormone receptor.

As indicated above, the term "neural growth hormone receptor" is used in this widest possible sense to cover all receptors on neuronal cell populations which growth hormone is capable of binding to and/or activating. Two such receptors are growth hormone receptor (GHR) and prolactin receptor (PRL-R). In particular, the term "neural growth hormone receptor" covers the human GHR and human PRL-R.

The human growth hormone receptor (GHR) is a 620 amino acid single chain protein containing a glycosylated 246 amino acid extracellular ligand binding domain, a single 24 amino acid transmembrane domain and a 350 amino acid cytoplasmic domain (Postel-Vinay and Kelly (1996) *Baillieres Clinical Endocrinology and Metabolism* 10:323). The GHR monomer binds to a single growth hormone (GH) by binding site 1, a second GHR is then required to bind to binding site 2 on the same GH after which the receptor dimerises and signal transduction occurs. Signal transduction involves the activation of cytoplasmic kinases resulting in the phosphorylation of numerous cytoplasmic peptides.

The human prolactin receptor (PRL-R) is a 590 amino acid single chain polypeptide with a glycosylated 210 amino acid extracellular ligand binding domain, a single 24 amino acid transmembrane domain and an intracellular domain of 358 amino acids. The PRL-R monomer binds to a single prolactin (PRL). A second PRL-R is then required to bind to the same PRL after which the receptor dimerises and signal transduction occurs. Signal transduction involves the activation of cytoplasmic kinases resulting in the phosphorylation of numerous cytoplasmic peptides in a mechanism very similar to the GHR.

A second short form of the PRL-R has also been characterised (Kelly et al (1991) *Endocrine Reviews* 12:235). This receptor is the same as the long version of the receptor in the extracellular and transmembrane regions but has much smaller cytoplasmic domain of only 57 amino acids.

This leads to the applicants second approach to neuroprotection and in particular neuronal rescue. This approach focuses upon neural growth hormone receptors as defined above and upon effecting neuroprotection through the use of agents which both bind to and activate these receptors.

It will be appreciated that growth hormone and its analogs are agents which achieve this. Indeed, the use of growth hormone and growth hormone analogs represents a preferred aspect of the invention. However, it should be appreciated that this approach is not restricted to the use of growth hormone and its analogs but also extends to any ligand which fulfils the functional requirement of both binding to and activating (stimulating) the neural growth hormone receptors. Implicit in this will be the ability of the ligand to effect the initiation of intracellular signalling.

Examples of such ligands are prolactin and analogs of prolactin and placental lactogen and analogs of placental lactogen. These are also capable of binding to and activating neural growth hormone receptors (Lowman et al (1991), *J. Biol. Chem.* 266:10982).

Other stimulatory ligands can be identified by a screening protocol employing at least the ligand binding domain of a neural growth hormone receptor. This screening method can, for example, utilise the expression of the neural growth hormone receptor in Xenopus oocytes using standard recombinant DNA methods and measurement of the receptor-mediated signal transduction evoked by stimulatory ligands. Further classical "grind and bind" ligand-binding experiments can also be utilised. Here, whole brain or specific brain regions are homogenised and specific-binding of compounds to the neural growth hormone receptor characterised. This technique allows further characterisation of specificity and affinity (potency) of the compound for the receptor complex (Frielle et al (1989) *Clin. Chem.* 35(5):721-725).

The methods of the invention have therapeutic effect. By "therapeutic effect" is meant any enhanced survival, proliferation and/or neurite outgrowth of neurons following an insult beyond that which occurs without administration of the therapeutic agent. By "enhanced neuronal survival" is intended that the administration of a therapeutic agent decreases neuronal loss by at least about 1-10%, preferably about 10%-50%, more preferably about 10%-50%, more preferably about 10%-90%, and most preferably greater than 90% beyond that which occurs without the administration of the agent.

Methods to quantify the extent of neural damage and to determine if neuronal survival was enhanced following the administration of a therapeutic agent are well known to those skilled in the art. Such methods include, but are not limited to, histological methods, molecular marker assays, and functional/behaviour analysis. For example, after ischemic injury, there is a significant increase in the density of omega 3 (peripheral-type benzodiazepine) binding sites (Benazodes, J. et al. (1990) *Brain Res.* 522:275-289). Methods to detect omega 3 sites are known and can be used to determine the extent of cerebral ischemia damage. See for example, Gotti, B. et al (1990) *Brain Res.* 522:290-307 and references cited therein. Alternatively, Growth Associated Protein-43 (GAP-43) can be used as a marker for new axonal growth following a CNS insult. See, for example, Stroemer et al (1995) *Stroke* 26:2135-2144, Vaudano et al (1995) *J. Neurosci* 15:3594-3611. The therapeutic effect may also be measured by improved patient motor skills, cognitive function, sensory perception, speech and/or a decrease in the propensity to seizure. Such functional/behaviour tests used to assess sensorimotor and reflex function are described in, for example, Bederson et al (1986) *Stroke* 17:472-476, DeRyck et al (1992) *Brain Res* 573:44-60, Markgraf et al (1992) *Brain Res.* 575:238-246, Alexis et al (1995) *Stroke* 26:2338-2346. Enhancement of neuronal survival may also be measured using the Scandinavian Stroke Scale (SSS) or the Barthel Index.

For the intended therapeutic application, the active compound (growth hormone, analog or ligand) will be formulated as a medicament. The details of the formulation will ultimately depend upon the neuroprotective effect to be induced. Where the neuroprotective effect is a neuronal rescue effect, the formulation will be largely dependent upon the insult to be remedied and the route of administration but will usually include a combination of the active compound with a suitable carrier, vehicle or diluent. Those skilled in the art are familiar with appropriate carriers, vehicles or diluents for each of the commonly employed methods of administration.

To be effective as a neuroprotective agent, a variety of administration routes can be used. Examples include lumbar puncture, intracerebroventricularly (ICV), intraventricular administration involving neurosurgical insertion of a ventricular cannular with an abdominal pump and reservoir and intraparenchymal. In addition, administration of the active compound directed to the CNS may be achieved through the olfactory neural pathway. See, for example, U.S. Pat. No. 5,624,898.

Dosage rates will also be formulation- and condition-dependent. However, by way of example, the recommended dosage rate of growth hormone formulated for injection would be in the range of 0.01 µg/100 g upwards.

The invention, in its various aspects, will now be illustrated by the experimental section which follows. It will however be appreciated that the experiments are non-limiting.

EXPERIMENTAL

Materials and Methods

Animal Preparation

The following experimental procedures followed guidelines approved by the University of Auckland Animal Ethics Committee. Weaned 21 day old Wistar rats, weighing between 40 and 50 g, were maintained on a 12 hour light and dark cycle and given free access to food and water throughout the study. The rats were paired by sex and weight and randomly assigned to either the treatment or control groups. HI injury was induced using a modified version of the Levine rat preparation as described previously (Sirimanne et al., J Neuroscience Methods, 55: 7-14, 1994). Briefly, the rats were anaesthetised and maintained on a 2% halothane/oxygen mixture and the right carotid artery ligated following exposure through a midventral neck incision. After surgery the rats were allowed to recover for 2 hours in a carefully controlled environment of 34° C. with 85+5% relative humidity. They were then exposed to 15 minute hypoxia (8% oxygen in nitrogen).

Treatment

Commencing 2 hours after the end of hypoxia, rats in the treatment group (n=12) received 20% g recombinant rat growth hormone in a 10 µl infusion, the control group received vehicle only. The infusion procedure was performed under heat lamps to prevent the animals from cooling. All solutions and needles were prepared and kept under aseptic conditions.

The rats were lightly anaesthetized again using 0.15 ml Saffan™ (Pitman-Moore Ltd, NZ). The infusion was made into the right lateral cerebral ventricle guided by a metal cap fitted over the rat head using a modified technique originally described by Jirikowski (J Neuroscience Methods, 42: 115-118, 1992), in order to ensure correct placement of the infusion needle. Recombinant rat growth hormone (2 mg/ml in 8.77 mg/ml NaCl, 2.5 mg/ml phenol, 2.0 mg/ml polysorbate 20 and 10 mM sodium citrate pH 6.0) or vehicle only was administered in a single dose at a rate of 1.0 µl /minute controlled by a calibrated microinfusion pump. The infusion needles were left in place a further 3 minutes to prevent backflow.

CSP Sampling

Three days after hypoxia cerebrospinal fluid (CSF) samples were taken. The rats were anaesthetised under Saffan anaesthesia and maintained on 2% halothane. They were then placed in a stereotaxic frame with the head flexed forward to allow blunt dissection of the muscle over the cisterna magna in order to expose the dura. A fine 30 gauge needle was then used to extract CSF with the aid of a binocular magnifier. The rats were euthanised by an overdose of sodium pentobarbitol administered ip and blood samples taken directly from the heart.

Histology

Brains were collected for histological processing after in situ fixation by transcardial perfusion with saline followed by a freshly prepared modified Bouin's solution (0.1M PBS, 4% paraformaldehyde [w/v], 0.08% glutaraldehyde [v/v], 15% picric acid [v/v of saturated solution]). Brains were removed, weighed and left in modified Bouin's solution overnight at room temperature. The following day the brains were placed in 70% ethanol for 3-4 days. The ethanol was replaced with fresh solution daily. The brains were then processed for paraffin embedding (dehydration through a graded series of ethanols, delipidation in chloroforn, infiltration with paraffin wax, blocking in paraffin wax). Eight 4 µm sections were cut from the tissue and placed on to poly-L-lysine pre-coated slides. Sections were stained using acid-fuschin/thionin.

Neuronal Scoring Procedure

Neural outcome was assessed using two levels in each brain; at the mid level of the striatum (Bregma +0.8 mm) and at the mid level of the dorsal horn of the hippocampus (Bregma −3.3). Neuronal outcome was assessed using two techniques:

1) Scoring in the Cortex and Hippocampus:

The frontoparietal cortex and the hippocampus were assessed by a blinded assessor for neuronal score using a standard five point neuronal loss score (Williams et al., Pediatric Research, 27: 561-565, 1990): 4=no damage, 3=0-10% cell loss, 2=11 to 50% cell loss, 1=51-90% cell loss, 0=>90% cell loss.

The cortex was scored at the level of the striatum (Bregma +8.0 mm) and at the level of the dorsal horn of the hippocampus (Bregma −3.3) and was divided into 5 regions. The hippocampus was scored in the CA1/2, CA3 and dentate gyrus separately. The neuronal scores were then combined for each structure and compared between treatment groups.

2) Scoring in the Striatum and Thalamus:

Four regions each of the striatum and thalamus were scored using an ocular micrometer on a light microscope at 200× magnification. Each region was counted using 4 grids of the micrometer at 200 $\mu m^2$/grid. Healthy neurons were counted in identical regions in the injured and contralateral hemisphere of each brain and % survival was calculated according to the following: counts RHS/counts LHS×100 for each region. The survival scores relating to each structure were then combined and compared between the treatment and control groups.

Radioimunoassay for IGF-1 in Plasma and CSF

IGF-1 in blood plasma and CSF were measured using an IGF binding protein (IGFBP) blocked radioimunoassay (RIA) first described by Blum and Breier (Growth Regulation, 4: 11-19, [1994]). A polyclonal antibody (#878/4) raised in New Zealand white rabbits which has a very high affinity and specificity for IGF-1 and low cross-reactivity with IGF-II (0.01%) was used. This assay utilises a non-extraction process with samples diluted in acidic buffer and co-incubated with an excess of IGF-II. Dilution at pH 2.8 followed by addition of IGF-II serves to functionally block binding protein interference.

Plasma was diluted (1:200-1:400) in acidic buffer (20 mM sodium phosphate pH 2.8, 0.1 mM NaCl, 0.1% BSA, 0.02% $NaN_3$, 0.1% triton X-100) and CSF samples were diluted (1:11) in 0.5M sodium phosphate, 1% BSA, 1% triton X-100, 0.1% $NaN_3$, 1 mM PMSF, pH 1.25 in order to dissociate IGFs from IGFBPs. The primaryy antibody, with IGF-II in excess at 25 ng/tube, was diluted in a buffer that re-neutralised the pH (100 mM sodium phosphate [pH7.8], 40 mM NaCl, 0.02% $NaN_3$, 0.2% BSA, 0.1% triton X-100) to an initial working dilution of 1:50000). 0.1 ml of diluted sample, control, or standard (rh-IGF-1, Genentech, San Fransisco) was incubated with 0.1 ml of antibody-IGF-II solution and 0.1 ml $^{125}I$-IGF-1 at 15-20000 counts per tube. After incubation for 48 hours at 4° C., 1 ml of the secondary antibody complex was added and tubes incubated for a further 1 hour at room temperature. Following centrifugation at 3800 rpm/30 min at 4° C., tubes were decanted and the pellet counted by gamma counter.

Iodination of rh-IGF-I was performed using a modification of the Chloramine-T method of Hunter and Greenwood (Biochemical Journal, 91: 43-56, 1964). The validation of this assay system was performed according to the recommendations of the Third International Symposium on Insulin-Like Growth Factors (Bang et al., Endocrinology, 136: 816-81, [1995]) including parallel displacement to the standard curve of CSF and recoveries of cold IGF-I. Recovery of unlabelled IGF-I in CSF was 89.6% (n=2). The ED-50 was 0.1 ng/tube and the intra- and inter-assay coefficients of variation were 5% and 9% respectively.

Statistics

The data was analysed using paired t-tests or the non-parametric equivalent, Wilcoxon signed rank test. Calculations were performed using Sigmastat™ v2.0 (Jandel Scientific, San Rafael, California). All results are expressed as mean±sem.

Results

Figure 2:
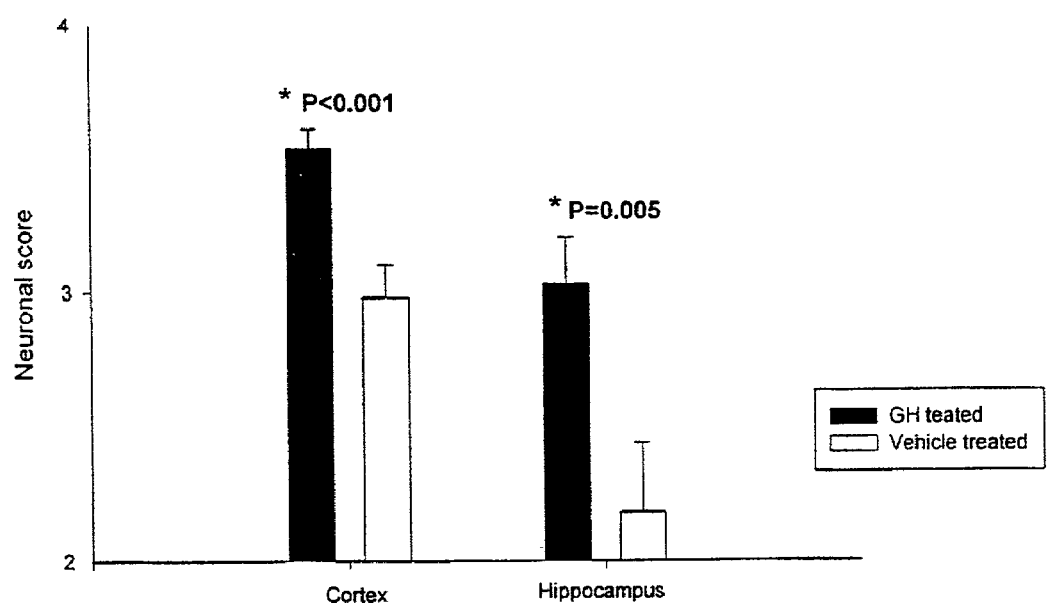
FIG. 2 shows the effect of ICV rat growth hormone treatment on neuronal score following moderate HI.
Figure 3:
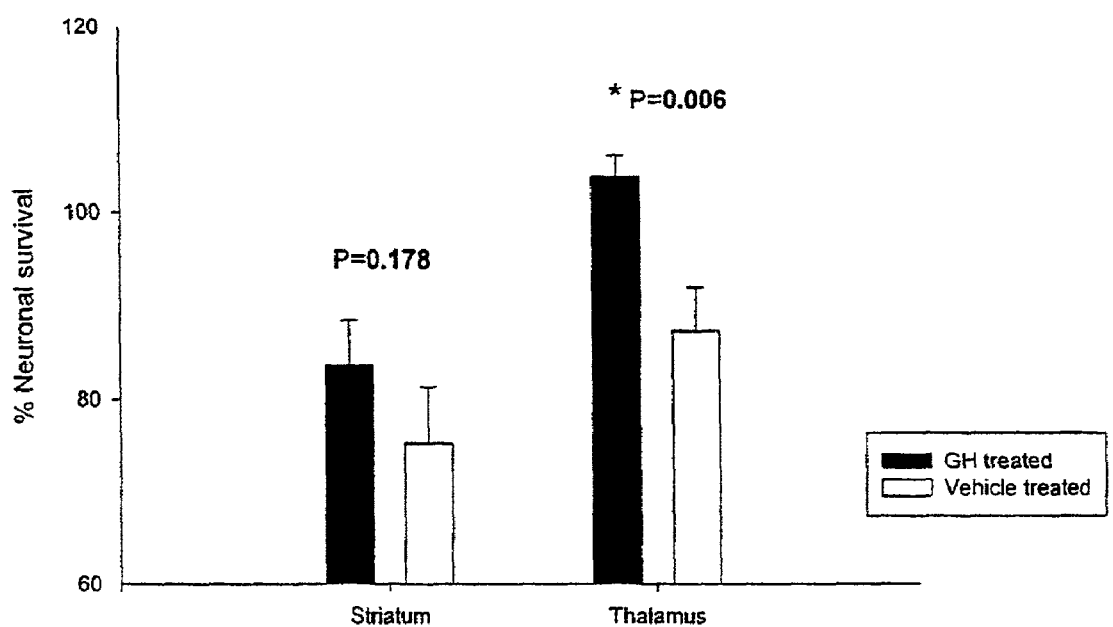
FIG. 3 shows the effect of ICV rat growth hormone treatment on neuronal survival following moderate HI.

The results are shown in FIGS. 1-3.

Growth hormone treatment had no effect on brain weight compared to vehicle only treated animals at post mortem (1.432±0.032 vs 1.455±0.028 g).

Growth hormone treatment caused a trend towards a reduction in the fall in serum IGF-1 caused by the HI injury (159±7.3 vs 135.8±11.7 ng/ml, p=0.068). CSF IGF-1 levels were much lower than those in plasma. CSF IGF-1 levels were unchanged by the growth hormone treatment (3.82±0.35 vs 3.86±0.27 ng/ml). This can be seen in FIG. 1.

Cortical neuronal score was significantly improved by growth hormone treatment. The combined score for all five cortical regions at the levels of the striatum and hippocampus was (3.54±0.074 vs 2.98±0.124, p<0.001). This is shown in FIG. 2.

Hippocampal neuronal score was significantly improved by growth hormone treatment. The combined score for CA1/2, CA3 and the dentate gyrus was (3.03±0.176 vs 1.818±0.259, p=0.005). This is shown in FIG. 2.

The neuronal survival score for the dorsolateral thalamus was significantly improved by growth hormone treatment. The combined score of the four areas counted and compared to the contralateral hemisphere was (104±2.18 vs 87.4±4.67%, p=0.006). This is shown in FIG. 3.

The neuronal survival score for the dorsolateral striatum was not significantly improved by the growth hormone treatment. The combined score of the four areas counted and compared to the contralateral hemisphere was (83.8±4.7 vs 75.3+±6.1%, p=0.178). This is shown in FIG. 3.

Conclusions

Growth hormone administered centrally is effective as a neuronal rescue agent. The neuronal rescue effect occurred without a concurrent increase in CSF-IGF-1, demonstrating the neuroprotective effect is independent of IGF-1.

Growth hormone is effective as a neuronal rescue agent in regions of the brain where the endogenous growth hormone receptor is expressed (cortex, hippocampus and thalamus) and not in areas where it is not (striatum). This indicates that the neuroprotective effect of GH is operating via either the growth hormone receptor or the prolactin receptor.

INDUSTRIAL APPLICATION

The invention therefore provides new approaches to neuroprotection. In particular, it provides new approaches to neuronal rescue.

The approaches of the invention have application in both therapy and prophylaxis. In particular, they have application in the treatment of patients who have suffered neuronal insult, including by injury, degenerative diseases and disorders, motor diseases and disorders, demyelinating diseases and disorders, neurological syndromes, eye diseases and sleep disorders. Specifically contemplated are the following:

Injury

Stroke, traumatic brain injury, asphyxia, spinal injuries and CO toxicity.

Degenerative Diseases and Disorders

Familial and non-familial Alzheimer's disease, multi-infarct dementia, frontal lobe dementia of the non-Alzheimer-type, Pick's disease, Huntington's disease, Werdnig Hoffmann disease, Wernicke's encephalopathy, Ataxia-telangiectasia, Corticobasal degeneration, Down's syndrome, Rett syndrome, IUGR, Alper's disease, Steele-Richardson-Olszewski syndrome, temporal lobe epilepsy, status epilepticus and undefined mental retardation.

Motor Diseases and Disorders

Spinocerebellar ataxia, progressive myoclonic ataxic syndrome, Leigh's disease, multiple system atrophy, the cerebral palsies, Friedeich's ataxia, pure hereditary spastic paraplegia, spinal muscular atrophies, diabetic neuropathy, hereditary sensory neuropathy type I, ALS, chronic idiopathic ataxic neuropathy, Tangier disease.

Demyelinating Diseases and Disorders

Inflammatory involvement: acute disseminated encephalomyelitis, optic neuritis, transverse myelitis, Devic's disease, the leucodystrophies, Multiple Sclerosis; Non-inflammatory involvement: Progressive multifocal leucoencephalopathy, central pontine myelinolysis.

Neurological Syndromes

Foetal alcohol syndrome, Autism and Myoclonic ataxia.

Eye Diseases

Glaucoma

Sleep Disorders

Narcolepsy

Further, while the growth hormone/growth hormone receptor approach of the invention can be employed alone in the above therapies, it is also contemplated that a combination therapy approach can be taken. This latter approach involves administering, in particular, growth hormone or an analog/ligand thereof in combination with a secondary neuroprotective agent. This secondary neuroprotective agent will generally be protective, at least in part, of a population neuronal cells which is distinct from the population of neuronal cells which are protected by growth hormone and its analogs/ligands.

Secondary neuroprotective agents may be selected from, but not limited to, the group comprising growth factors. By "growth factors" is meant an extracellular polypeptide-signaling molecule that stimulates a cell to grow or proliferate. Preferred growth factors are those to which a broad range of cell types respond. Examples of neurotrophic growth factors include, but are not limited to, fibroblast growth factor family members such as basic fibroblast growth factor (bFGF) (Abraham et al (1986) *Science* 233: 545-48), acidic fibroblast growth factor (aFGF) (Jaye et al (1986) *Science* 233:541-45), the hst/Kfgf gene product, FGF-3 (Dickson et al (1987) *Nature* 326-833), FGF-4 (Zhan et al (1988) *Mol. Cell. Biol.* 8:3487-3495), FGF-6 (deLapeyriere et al 91990) *Oncogene* 5:823-831), Keratinocyte growth factor (KGF) (Finch et al (1989) *Science* 245:752-755) and androgen-induced growth factor (AIGF) (Tanaka et al (1992) *Proc. Natl. Acad. Sci.* USA 89:8928-8923). Additional members of the FGF family include, for example, int-2, fibroblast growth factor homologous factor-1 (FHF-1) (U.S. Pat. No. 5,872,226), FHF-2 (U.S. Pat. No. 5,876,697), FHF-3 and FHF-4 (Smallwood et al (1996) *Proc. Natl. Acad. Sci.* USA 93:9850-9857), karatinocyte growth factor 2 (Emoto et al (1997) *J. Biol Chem* 272:23191-23194), glia-activating factor (Miyamoto et al (1993) *Mol. Cell. Biol.* 13:4251-4259), FGF-18 (Hu et al (1998) *Mol Cell Biol* 18:6063-6074), and FGF-16 (Miyake et al (1988) *Biochem. Biophys. Res. Commun* 243:148-152.

Additional secondary neuroprotective agents include ciliary neurotrophic factor (CNTF), nerve growth factor (NGF) (Seiler, M. (1984) *Brain Research* 300:33-39; Hagg T, et al (1988) *Exp Neurol* 101:303-312; Kromer L F (1987) *Science* 235:214-216; and Hagg T et al (1990) *J. Neurosci* 10 (9)3087-3092), brain derived neurotrophic factor (BDNF) (Kiprianova, I et al (1999) *J. Neurosci. Res.* 56:21-27), Neurotrophin 3 (NT3), Neurotrophin 4 (NT4), transforming growth factor-β1 (TGF-β1) (Henrick-Noack, P et al (1996) *Stroke* 27:1609-14), bone morphogenic protein (BMP-2) (Hattori, A et al. (1999) *J. Neurochem* 72:2264-71), glial-cell line derived neurotrophic factor (GDNF) (Miyazaki, H et al (1999) *Neuroscience* 89:643-7), activity-dependent neurotrophic factor (ADNF) (Zamostiano, R et al (1999) *Neurosci Letter* 264:9-12), cytokine leukemia inhibiting factor (LIF) (Blesch, A et al (1999) *J. Neurosci.* 19:3356-66), oncostatin M, interleukin, and the insulin-like growth factors 1 and 2.

Other forms of secondary neuroprotective agents include, for example, clomethiazole (Zendra) (Marshal, J W et al (1999) *Exp Neurol* 156:121-9); kynurenic acid (KYNA) (Salvati, P et al (1999) *Prog. Neuropsychopharmacol Biol Psychiatry* 23:741-52), Semax (Miasoedova, N. F. et al (1999) *Zh Nevrol Psikhiatr Imss Korsakova* 99:15-19), FK506 (tacrolimus) (Gold, B G et al (1999) *J. Pharmacol. Exp. Ther.* 289:1202-10), L-threo-1-phenyl-2-decanoylamino-3-morpholino-1-propanol (Inokuchi, J. et al (1998) *Act Biochim Pol* 45:479-92), andrenocorticotropin-(4-9) analoge (ORG 2766) and dizolcipine (MK-801) (Herz, R C et al (1998) *Eur. J. Pharmacol* 346:159-65), cerebral interleukin-6) (Loddick, S A et al (1998), *J. Cereb Blood Flow Metab* 18:176-9), selegiline (Semkova, I et al (1996) *Eur. J. Pharmacol* 315:19-30), MK-801 (Barth, A et al (1996), *Neuro Report* 7:1461-4; glutamate antagonists such as, NPS1506, GV1505260, MK801 (Baumgartner, W A et al (1999) *Ann Thorac Surg* 67:1871-3), GV150526 (Dyker, A G et al (1999) *Stroke* 30:986-92); AMPA antagonists such as NBQX (Baumgartner, W A (1999) et al. *Ann Thora Surg* 67:1871-3, PD152247 (PNQX) (Schielke, G P et al (1999) *Stroke* 30:1472-7), SPD 502 (Nielsen, E O et al (1999) *J Pharmacol Exp Ther* 289:1492-501), LY303070 and LY300164 (May, P C et al (1999) *Neuroscience Lett* 262: 219-221).

In one embodiment, the secondary neuroprotective agent is IGF-1 and/or a biologically active variant of IGF-1. IGF-1 is a 70 amino acid neurotrophic polypeptide hormone that is widely distributed in the central nervous system and exhibits both insulin-like and mitogenic growth biological activities (Baskin, D G et al (1988) *Trends in Neuroscience* 11:107-111). In vitro studies have demonstrated that the neuroprotective effects of IGF-1 extend to several types of neurons in the CNS (Knusel et al (1990) *J Neurosi.* 10:558-570, Svezic and Schubert (1990) *Biochem. Biophys. Res. Commun.* 172:54-60 McMorris and Dubois (1988), *J Neurosci Res.* 21:199-209). In addition, in vivo studies using various experimental animal models have shown exogenous administration of IGF-1 soon after a CNS insult elicits a neuroprotective effect (Guan et al (1993) *J. Cereb Blood Flow Metab* 13:609-616 and Johnston et al (1996) *J. Clin. Invest.* 97:300-308, U.S. Pat. No. 5,861,373, U.S. Pat. No. 5,093, 317, U.S. Pat. No. 5,093,317, U.S. Pat. No. 5,776,897 and references cited therein.

Preferred secondary neuroprotective agents include IGF-1, GPE, activin, NGF, TGF-β growth hormone binding protein, IGF-binding proteins (especially IGFBP-3), and bFGF.

Specific combinations include growth hormone and one or more of GPE, IGF-1 and activin for use in the therapy of Huntington's disease or Alzheimer's disease; growth hormone and IGF-1 for use in the therapy of corticobasal degeneration or Steele-Richardson-Olszewski syndrome; growth hormone and one or both of GPE and IGF-1 for use in the therapy of Devic's disease or Picks disease; and growth hormone and one or both of activin and IGF-1 for use in the therapy of diabetic neuropathy.

Where the combination therapy approach is viewed as desirable, the respective active agents can be formulated for co-administration, including as a single medicament. The invention therefore provides such neuroprotective medicaments which comprise, in combination, growth hormone or an analog thereof together with one or more of the secondary neuroprotective agents above other than IGF-1, particularly one or more of GPE, activin, NGF, TGF-β and bFGF. Where desirable, such medicaments can further include IGF-1.

Such medicaments can be prepared in any conventional manner, and can again include standard pharmaceutically-acceptable vehicles, carriers or diluents.

Those persons skilled in the art will appreciate that the above description is provided by way of example only.

REFERENCES

Andronikof-Sanglade, A., Fjellestad-Paulsen, A., Ricard-Malivoir, S., and Evain-Brion, D. (1997). Specific abnormalities in a visual motor psychological test in short children with abnormal growth hormone secretion. *Acta Paediatnca* 86[2], 154-159.

Bartlett, W. P., Li, X. S., Williams, M., and Benkovic, S. (1991). Localisation of insulin-like growth factor-I mRNA in murine central nervous system during postnatal development. *Developmental Biology* 147, 239-250.

Beck, K. D., Powellbraxton, L., Widmer, H.R., Valverde, J. and Hefti, F. (1995). IGF-1 gene disruption results in reduced brain size, CNS hypomyelination, and loss of hippocampal granule and striatal parvalbumin-containing neurons. *Neuron* 14, 717-730.

Bondy, C. and Lee, W. H. (1993) Correlation between insulin-like growth factor (IGF) binding protein-5 and IGF-1 gene expression during brain development. *Journal of Neuroscience* 13, 5092-5104.

Burton, K. A. Kabigting, E. B., Clifton, D. K. and Steiner, R. A. (1992). Growth hormone receptor messenger ribonucleic acid distribution in the adult male rat brain and its colocalisation in hypothalamic somatostatin neurons. *Endrocrinology* 131, 958-963.

Garofalo, R. S. and Rosen, O. M. (1989). Insulin and insulin-like growth factor 1 (IGF-1) receptors during central nervous system development: expression of two immunologically distinct IGF-1 receptor beta subunits. *Molecular & Cellular Biology* 9, 2806-2817.

Lobie, P. E., Garcia Aragon, J., Lincoln, D. T., Barnard, R., Wilcox, J. N., and Waters, M. J. (1993). Localisation and ontogeny of growth hormone receptor gene expression in the central nervous system. *Developmental Brain Research* 74[2], 225-233.

Noguchi, T. (1991). Retarded cerebral growth of hormone-deficient mice. *Comparative Biochemistry & Physiology—C: Comparative Pharmacology & Toxicology* 98[1], 239-248.

Clark, R. G. and Robinson, I. C. A. F. (1996). Up and Down the Growth Hormone Cascade. *Cytokine and Growth Factor Retnews Vol* 7, No. 1 pp 65-80.

Bowers, C. Y. (1993). GH releasing peptides-structure and kinetics. *J. Paed. Endocrinology*, 6:21-31.

Clark, R. G., Robinson, I. C. A. F. (1996). Up and down the growth hormone cascade. *Cytokine and Growth Factor Reviews* 75 (1), 65-80.

Deghenghi, R., Cananzi, M. M., Torsello, A., Battisti, C., Muller, E. E., Locatelli, V. (1994). GH-releasing activity of hexarelin, a new growth hormone releasing peptide, in infant and adult rats. *Life Sci.* 54, 1321-1328.

Frielle, T. Caron, M. G., Leftowitz, R. J. (1989). Properties of the beta 1-and beta 2-adrenergic receptor subtypes revealed by molecular cloning. *Clinical Chemistry* 25 35(5): 721-5.

Frohman, L. A., Downs, T. R., Chomczynski, P. (1992). Regulation of growth-hormone secretion. *Front Neuroendocrinol* 13, 344-405.

Gillies, G. (1997). Somatostatin: the neuroendocrine story. *Trends in Pharmacological Science* 18 (3), 87-95.

Kelly, P. A., Dijane, J., Postel-Vinay, M-C., Ederly, M. (1991). The prolactin/growth hormone receptor family 12 (3), 235-251.

Lowman, H. B., Cunningham, B. C., Wells, J. A. (1991). Mutational analysis and protein engineering of receptor-binding determinants in human placental lactogen. *Journal of Biological Chemistry* 266, 10982-10988.

Maxwell, M., Allegra, C., MacGillivary, J., Hsu, D. W., Hedley-Whyte, E. T., Riskind, P,. Madsen, J. R., Black, P. M. (1998). Functional transplantation of the rat pituitary gland. *Neurosurger* 43 (5), 1157-1163.

McDowell, R. S., Elias, K. A., Stanley, M. S., et al. (1995). Growth hormone secretagogues: characterization, efficacy and minimal bioactive conformation. *Proc. Natl. Acad. Sci. USA* 92, 11165-11169.

Patchett, A. A., Nargund, R. P., Tata, J. R. et al. (1995). Design and biological activities of L-163,191 (MK-0677): a potent, orally active growth hormone secretagogue. *Proc. Natl. Acad. Sci. USA* 92, 7001-7005.

Postel-Vinay, M-C., and Kelly, P. A. (1996). Growth hormone receptor signalling. *Baillieres Clinical Endocrinology and Metabolism* 10, 323-336.

Guan et al (1993) *J. Cereb. Blood Flow Metab.* 13:609-616.

Knusel et al (1990) *J. Neurosci.* 10:558-570.

We claim:

1. A method for inducing a neuroprotective effect of rescuing neurons destined to degenerate or die as a result of hypoxia or ischemia in a brain of a patient, comprising administering growth hormone centrally to the brain of the patient.

2. The method of claim 1, where the neural rescue effect is the rescue of neurons otherwise destined to die as the result of a prior hypoxia or ischema.

3. The method of claim 1 further comprising administering to said patient, a pharmaceutically effective amount of a substance selected from the group consisting of growth hormone releasing peptides (GHRP), GHRP-1, GHRP-2, GHRP-6, Hexarel in, G-7039, G-7502, L-692,429, L-692, 585, L-163,191, growth hormone releasing hormone (GHRH), prolactin, placental lactogen and somatostatin (somatotropin release inhibitory factor; SRIF).

4. The method of claim 1 further comprising administering a secondary neuroprotective agent.

5. The method of claim 4 where the secondary neuroprotective agent is selected from the group consisting of IGF-1, GPE, activin, NGF, TGF-$\beta$, growth hormone binding proteins, IGF-binding proteins and bFGF.

6. The method of claim 1 wherein said patient suffers from stroke.

7. The method of claim 1, wherein the route of administration of said growth hormone is via lumbar, intracerebroventricular (ICV), intraventricular, intraparenchymal, or olfactory neural route.

* * * * *

UNITED STATES PATENT AND TRADEMARK OFFICE
CERTIFICATE OF CORRECTION

| | | |
|---|---|---|
| PATENT NO. | : 7,304,029 B1 | Page 1 of 1 |
| APPLICATION NO. | : 09/786982 | |
| DATED | : December 4, 2007 | |
| INVENTOR(S) | : Scheepens et al. | |

It is certified that error appears in the above-identified patent and that said Letters Patent is hereby corrected as shown below:

Column 1, lines 2-4, after the title and before the first paragraph, insert:

--This application is a 371 of international patent application number PCT/US1999/00147, filed September 3, 1999, which claims priority to New Zealand provisional patent application number 331,719, filed September 3, 1998. Both of these applications are herein incorporated by reference.--

Signed and Sealed this

Twelfth Day of August, 2008

JON W. DUDAS
*Director of the United States Patent and Trademark Office*